United States Patent [19]

Cohen et al.

[11] Patent Number: 4,930,517

[45] Date of Patent: Jun. 5, 1990

[54] METHOD AND APPARATUS FOR PHYSIOLOGIC SYSTEM IDENTIFICATION

[75] Inventors: Richard J. Cohen, Waban; Marvin L. Appel, Cambridge; Ronald D. Berger, Brookline, all of Mass.

[73] Assignee: Massachusetts Institute of Technology, Cambridge, Mass.

[21] Appl. No.: 343,404

[22] Filed: Apr. 25, 1989

[51] Int. Cl.$^5$ ............................................. A61B 5/02
[52] U.S. Cl. ................................... 128/671; 128/695; 364/413.03
[58] Field of Search ...................... 128/671, 695, 696; 364/413.01, 413.02, 413.03, 413.04, 413.05, 413.06

[56] References Cited

U.S. PATENT DOCUMENTS

| | | | |
|---|---|---|---|
| 4,777,960 | 10/1988 | Berger et al. | 128/706 |
| 4,793,361 | 12/1988 | DuFault | 128/696 |
| 4,812,976 | 3/1989 | Lundy | 364/413.06 |

OTHER PUBLICATIONS

R. O. Kenet, "Closed-Loop Identification of Hemodynamic Control Systems", Ph.D. Thesis, Yale University, Jun. 1983.
G. Baselli et al, *IEEE Transactions on Biomedical Engineering*, "Cardiovascular Variability Signals: Towards the Identification of a Closed-Loop Model of the Neural Control Mechanisms", vol. 35, No. 12, Dec. 1988, pp. 1033-1046.
S. Kalli et al., *Proceedings of the Third International Conference on Measurement in Clinical Medicine*, "Applying a Multivariate Autoregressive Model to Describe Interactions Between Blood Pressure and Heart Rate", Edinburgh, 1986, pp. 77-82.
S. Kalli et al, *Computers in Cardiology, Proceedings IEEE Computer Society*, "Analysis of Blood Pressure and Heart Rate Variability Using Multivariate Autoregressive Modelling", 1986, p. 4.
R. D. Berger et al., *American Journ. of Physiology*, "Transfer Function Analysis of Autonomic Regulation", vol. 256, *Heart and Circulatory Physiology*, vol. 25, pp. H142-H152 (1989).
R. I. Kitney et al., *Transactions of the Institute of Measurement and Control*, "System Identification of the Blood Pressure Control System by Low Frequency Neural Stimulation", vol. 4, No. 4, Oct.-Dec. 1982, p. 202-203.
J. P. Saul et al., *American Journ. of Physiology*, "Transfer Function Analysis of Autonomic Regulation II. Respiratory Sinus Arrhythmia", vol. 256, *Heart Circ. Physiology*, vol. 25, 1989, pp. H153-H161.
B. K. Walker et al, *IFAC Symposium on Identification and System Parameter Estimation*, "Parameter Identification and Adaptive Control for Blood Pressure", Washington, D.C., 1982, pp. 1413-1418.
B. C. McInnis et al., *IFAC Symposium on Identification and System Parameter Estimation*, "Adaptive Pole Assignment Control of Blood Pressure Using Bilinear Models", York, 1985, pp. 1209-1212.
D. A. Linkens, *IFAC Symposium on Identification and System Parameter Estimation*, "Identification of Respiratory and Cardiovascular Systems", York, 1985, pp. 55-57.

*Primary Examiner*—Francis Jaworski
*Assistant Examiner*—George Manuel
*Attorney, Agent, or Firm*—Choate, Hall & Stewart

[57] ABSTRACT

A method and apparatus for estimating transfer functions among multiple physiologic or biologic signals in the presence of feedback. The invention comprises the injection of broad band purturbation into one or more of the subsystems under study, and measuring signals from the subsystems. These signals are transformed to generate a new set of n signals. Casual transfer functions between the signals and additive noise sources are used to represent the relationships between the n signals. Parametric system identification techniques are then used to characterize quantitatively at least two casual transfer functions and noise sources. This method and apparatus provides a powerful tool with which to characterize the interactions of subsystems in the presence of feedback.

42 Claims, 3 Drawing Sheets

Space tones evenly in time at 12/min. ~410

Space tones randomly but with a mean of 12/min. using a modified Poisson distribution with $\Delta t_{max}$ =15 sec and $\Delta t_{min}$ =1 sec. ~412

Subject breathes to tones for 13 minutes ~414

ECG, Instantaneous Lung Volume (ILV) and Arterial Blood Pressure (ABP) are recorded and sampled at 360 Hz with anti-aliasing filtering. ~416

Form time series of heart rate @2.8125 Hz. ~418

Synchronize with ABP and ILV time series. ~420

Subtract mean of signal from each point of signal and pad with zeroes for 1024 additional points. ~422

Take FFT of padded signal. ~424

Point by point multiply the FFT of one signal with the complex conjugate FFT of another signal in all pairwise permutations. ~426

Take inverse FFT to get $R_{ij}$ ~428

Form Normal Equations in terms of known $R_{ij}$ and unknown parameters. Find the values of the unknown parameters which minimize the noise functions for a given model order by solving the Normal Equations. ~430

Determine optimal model order. ~432

METHOD AND APPARATUS FOR PHYSIOLOGIC SYSTEM IDENTIFICATION

BACKGROUND OF THE INVENTION

This invention relates to method and apparatus for estimating transfer functions among multiple physiologic or biologic signals in the presence of feedback.

A living organism includes multiple physiological organ subsystems. While each of these subsystems performs a specific function, such as respiration or blood circulation, there is a complex interaction between them which adjusts their functioning. These adjustments adapt the organism to a variety of environmental conditions and tasks.

As an example, consider what occurs in the simple act of standing. A supine subject undergoes a variety of physiological adjustments when the subject stands up. Changing the direction of gravity results in a change in heart rate, blood pressure, and vascular tone. The physiological subsystems must come to a new equilibrium state that allows the subject to function under this new environmental condition. If, for example, vascular tone did not change upon standing, the blood would pool in the lower extremities. This pooling ultimately would result in a loss in consciousness as the brain is deprived of blood flow.

An understanding of the regulation of the physiology of the organism requires not only an understanding of each organ subsystem but also of their interactions. One difficulty is that each organ system is itself complex and any, in turn, consist of a large number of components. This complexity frequently makes a complete understanding of an organ subsystem impossible. However, the lack of understanding of the internal or fine-structure of an organ subsystem does not preclude an understanding of how that subsystem interacts with other organ subsystems.

The reason that the interactions may be studied without a detailed knowledge of the individual organ subsystems is that a complex system may be treated as a single unit or black-box about which nothing is known except for its stimulus (input) and response (output). By understanding the way a subsystem responds to a specific input, a mathematical description of that subsystem treated as a black-box may be developed. It so happens that, if the subsystem can be considered to have certain mathematical properties, the description developed for that one specific input is valid for all inputs.

This approach is reasonable in the study of physiological systems since it is actually only the stimuli and responses which are measured. For example, it is the heart rate (response) that is measured as a function of changes in arterial blood pressure (stimulus), and it is irrelevant that the functioning of the individual cell types of the heart cannot be determined. This systems approach to physiology has resulted in a greater understanding of the interactions between organ subsystems.

In order to characterize a black-box from input-output data, one must elicit the entire range of possible responses from the subsystem; such suitable inputs are called "informative". With real systems, it is often the case that the spontaneous fluctuations within the system are not informative. It is therefore necessary to enrich the inputs by adding exogenous broad-band noise in the form of external stimuli.

Many earlier efforts have been directed towards modeling the cardiovascular control system and estimating the transfer relations in the models. Robert Kenet, in his PhD thesis (Yale University, 1983), considered two transfer functions, heart rate to blood pressure and blood pressure to heart rate, operating in closed loop.

Kenet used parametric identification techniques but did not whiten the spontaneous heart rate fluctuations by introducing an external noise source. Instead, he analyzed data from dogs undergoing atrial fibrillation, which, although it does generate broadband ventricular heart rate, it essentially destroyed the baroreceptive feedback loop. Thus, Kenet was unable to accommodate both closed-loop physiologic function with broadband signals.

Another group used multivariate autoregressive modeling to analyze heart rate and blood pressure signals without explicitly measuring respiration and without enriching the spontaneous fluctuations. However, their method was less general than Kenet's because it did not allow poles in either of the transfer functions. (See *Analysis of Blood Pressure and Heart Rate Variability Using Multivariate Autoregressive Modeling*, Kalli, S, Suoranta, R, Jokipii, M, and Turjanmaa, V. Computers in Cardiology Proceedings, IEEE Computer Society (1986); *Applying a Multivariate Autoregressive Model to Describe Interactions Between Blood Pressure and Heart Rate*, Kalli, S, Suoranta, R and Jokipii, M., Proceedings of the Third International Conference on Measurement in Clinical Medicine, pp 77–82, Edinburgh; (1986)).

Baselli et al. used parametric techniques to identify a closed-loop model of cardiovascular control that incorporated heart rate, blood pressure and respiration signals, but, they too did not whiten the spontaneous fluctuations in heart rate, and therefore, their methodology does not allow reliable identification of the causal transfer functions under the usual conditions of narrow band spontaneous fluctuations. (See *Cardiovascular Variability Signals: Towards the Identification of a Closed-Loop Model of the Neural Control Mechanisms*, Baselli, G, Ceruttie, S, Civardi, S, Malliani, S and Pagani, S.) IEEE Transactions on Biomedical Engineering, 35, p. 1033–1046 (1988)).

Non-parametric (frequency domain) methods have also been applied to cardiovascular system identification. These methods do not permit the separate estimation of the feedforward (G) and feedback (H) components of a system. Instead, one can estimate only the overall closed loop transfer function of the form $G/(1+GH)$. In general there are many (G,H) pairs that are consistent with a given closed loop transfer function. (See *Transfer Function Analysis of Autonomic Regulation 1. Canine Atrial Rate Response*, Berger, R. D., Saul, J. P. and Cohen, R. J. American Journal of Physiology, vol. 256, Heart and Circulatory Physiology, vol. 25, pp H142–152, 1989) Berger et al. electrically stimulated either the vagus or sympathetic heart rate control systems in dogs at intervals generated by passing broadband frequency modulated noise through an integrate-and-fire filter. This experiment achieved broad-band, open loop stimulation of the cardiovascular system. Kitney et al. performed similar experiments on rabbits, using a pulse-frequency modulated pseudo-random binary sequence to stimulate the cardiac depressor nerve (baroreceptor afferent). (See *System Identification of the Blood Pressure Control System by Low Frequency Neural Stimulation*, Kitney, R. I. and Gerveshi, C. M. Transactions of the Institute of Measurement and Control, vol. 4, pp 203–212, (1982)).

A noninvasive method for broadening the frequency content of heart rate and blood pressure fluctuations by whitening the respiratory perturbations was described by Berger et al. in U.S. Pat. No. 4,777,960 and applied experimentally in *Transfer Function Analysis of Autonomic Regulation II. Respiratory Sinus Arrhythmia*, J. P. Saul, R. D. Berger, M. H. Chen, R. J. Cohen, American Journal of Physiology, Volume 256, (Heart Circ. Physiology 25), p. H153–H161, 1988. However, because this work did not address the causal relationship between signals it does not provide a methodology for separately identifying the feed-forward and feedback transfer functions in a closed-loop system.

Parametric system identification techniques have been applied to control anti-hypertensive drug delivery in response to changes in blood pressure. (*Parameter Identification and Adaptive Control for Blood Pressure*, Walker, B. K., Chia, T.-L., Stern, K. S. and Katona, P. G. IFAC Symposium on Identification and System Parameter Estimation, pp 1413–1418, (1982); *Adaptive Pole Assignment Control of Blood Pressures Using Bilinear Models*, McInnis, B. C., Deng, L-z and Vogt, R., IFAC Symposium on Identification and System Parameter Estimation, pp 1209–1212, (1985)). Approaches in this field have one common element: the input is the drug infusion and the output is blood pressure. The goal is to determine a feedback control law that adequately regulates arterial blood pressure, which involves first identifying the open-loop feedforward path (i.e.: how blood pressure responds to a unit drug infusion).

Finally, several groups have constructed mathematical models of circulatory regulation and of circulatory mechanics. These models are designed to reproduce phenomena observed in many data sets or in particular exemplary ones, but are not designed to be fit to any individual's data. In fact, it would be impossible to find a unique best fit of these models' parameters to any particular data record; that is, they are not identifiable. Although the mathematical descriptions these models offer may use linear system elements, they do not serve the same purpose as the present invention. (See *Identification of Respiratory and Cardiovascular Systems*, D. A. Linkens IFAC Sumposium on Identification and System Parameter Estimation, pp 55–67, (1985)).

The present invention teaches how noise injected into one or more inputs can be used in conjunction with parametric system identification techniques to identify the n(n-1) possible transfer relationships (transfer functions in the frequency domain or impulse or other driving signal responses in the time domain), that relate n signals by all possible feedback and feedforward paths. This for the first time allows one to identify accurately; physiological transfer functions in the presence of feedback. For the purposes of this discussion, the term transfer function will be used to mean transfer relationships both in the frequency and in the time domains.

SUMMARY OF THE INVENTION

The invention disclosed herein involves the measurement of physiological transfer functions by the injection of noise into one or more of the subsystems under study.

In one embodiment the transfer, functions describing the interaction of heart rate, instantaneous lung volume, and arterial blood pressure are estimated by solving the simultaneous equations describing the interaction of the signals. The injection of noise into the respiratory system is accomplished by having the subject undertake random interval breathing. In random interval breathing the subject inspires upon audio-cues, which are randomly distributed in time, but which are distributed so as to be Poisson about a given mean. This random interval breathing results in a broad-band additive noise with significant content at all physiologically relevant frequencies.

Because the input signal is broad-band, the transfer functions derived therefrom characterize the interactions of the systems accurately. Although the noise in injected into only one of the subsystems, a number of transfer functions are quickly and easily determined. This present invention provides a method of measuring physiological transfer functions as well as estimating the unmeasured noise signals and their power spectra. Thus, this invention provides a powerful method for the quantitative characterization of physiologic regulation which is of major importance in the clinical assessment of the cardiovascular and other systems.

DESCRIPTION OF THE PREFERRED EMBODIMENTS

The drawing is briefly described as follows.

Figure 1:
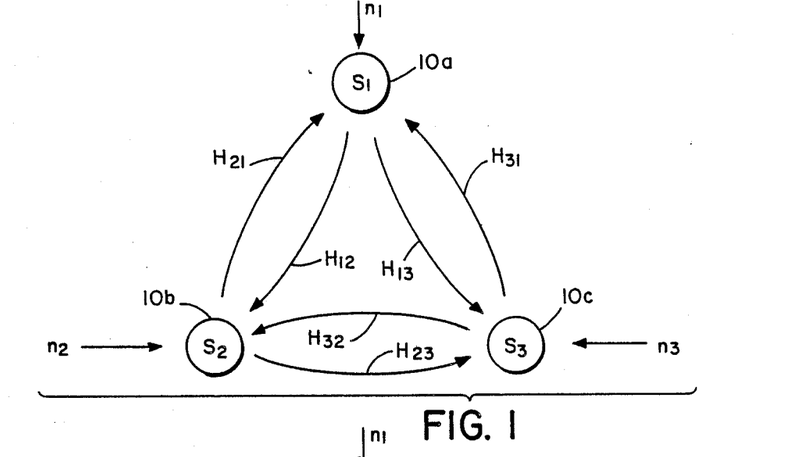
FIG. 1 is a generalized block diagram of a group of three interacting physiological subsystems indicating the parameters, the transfer functions, and the noise sources.

With reference to FIG. 1, a living organism consists of n (where n=3 for simplicity in illustrating the figure) interacting physiological subsystems 10a, 10b, 10c, each of which generates biological signals, $S_1$, $S_2$, $S_3$, and each of which has associated with it noise $N_1$, $N_2$, $N_3$. The noise source may represent internally generated intrinsic noise or externally applied perturbations. Signals that have associated with them intrinsic noise sources that are sufficiently independent and broad-band do not require perturbation by external broad-band noise sources. However, narrow-band signals may require perturbation by one or more external broad-band noise sources to facilitate system identification. In general, each subsystem 10 can be described by a number of related signals ($S_n$). For example, respiration could be described by respiratory frequency, tidal volume, or instantaneous lung volume. Such related signals might be measured using different transducers, or might be obtained by linear and/or nonlinear transformation of a single measured signal. For example, respiratory frequency and tidal volume can be derived from a nonlinear transformation of the instantaneous lung volume signal. Similarly, the heart rate is derived from a nonlinear transformation of the electrocardiogram signal. Generally, the signal which most closely reflects the desired features of the subsystem is used. If one wishes to utilize two or more signals related to a subsystem, this corresponds to conceptually dividing that subsystem into two or more subsystems for the purpose of analysis.

Each subsystem 10 may affect and may be affected by other subsystems 10. The manner in which each subsystem 10 affects another subsystem 10 is described mathematically by a transfer function ($H_{ij}$). The transfer function is a mathematical construct which relates the input of a system to its output. To determine the transfer function, it is necessary only to measure the input signal (x) and the output signal (y). The subscript ($i$) of the transfer function ($H_{ij}$) denotes the subsystem 10 doing the affecting, while the subscript ($j$) of the transfer function ($H_{ij}$) denotes the subsystem 10 affected. Therefore, $H_{12}$ signifies the transfer function describing the effect on subsystem 10b by subsystem 10a. Similarly, $H_{21}$ signifies the transfer function describing the effect upon subsystem 10a by subsystem 10b. Some of the transfer functions $H_{ij}$) may be zero. So, if subsystem 10b has an effect on subsystem 10a, but subsystem 10a does not affect subsystem 10b, the transfer function $H_{21}$ will be non-zero, but $H_{12}$ will be identically 0. If all the transfer functions are zero, then the subsystems 10a, b, c are independent and have no effect on each other.

In order to identify the six transfer functions and estimate the spectra of the three noise sources in FIG. 1, it is necessary to assume that there is no instantaneous feedback loop (i.e.: there are nonzero time delays in at least some of the transfer functions) and that the noise sources are linearly independent. If these conditions are not met then there is not a unique transfer function estimate for which the procedure works. Furthermore, for unbiased transfer functions estimates, the extent to which the noise sources are correlated with one another must be known and included in the model equations.

The number of transfer functions one can uniquely identify in the method of this invention is limited by the number of measured signals. In an actual biological system, of course, many more feedforward and feedback relations may actually exist. Thus, the transfer functions identified may necessarily include the contributions of a plurality of transfer relations in the actual system.

For example, the body regulates blood pressure by changing heart rate, peripheral resistance and venous tone. In a model of the system in which fluctuations in blood pressure and heart rate are explicitly represented but fluctuations in peripheral resistance and venous tone are not explicitly represented, the contributions of mechanisms involving adjustment of peripheral resistance and venous tone can be represented mathematically by blood pressure to blood pressure feedback. In the identification scheme of this invention such a separate blood pressure to blood pressure feedback loop could not be uniquely identified. Rather the effect of such feedback is to mimic poles in transfer functions where blood pressure sure is an output. Thus, without further information or assumptions it is impossible to distinguish the effects of poles in a transfer function in which a given signal is an output, from feedback from that signal back onto itself either directly or through a mechanism not accounted for in one's model.

This can be seen by actually writing out the equations for the discrete-time, linear time invariant system. Suppose that y(t) is an output, that x(t) is a known input. Then one might write $$y(t) = e(t) + \sum_{i=1}^{i=p} a_i y(t-i) + \sum_{i=0}^{i=m} b_i x(t-i)$$

where e(t) is the residual time series. Now suppose that the true system contains an input s(t) that is not acknowledged in the above model. The true system would be $$y(t) = e(t) + \sum_{i=1}^{i=p} a_i y(t-i) + \sum_{i=0}^{i=m} b_i x(t-i) + s(t)$$

Suppose further that s(t) represents an additional feedback mechanism for regulating y(t) so that $$s(t) = \sum_{i=1}^{i=n} c_i y(t-i) + w(t)$$

where w(t) is the residual for this feedback path. Then, substituting for s(t) in the true system equation gives $$y(t) = e(t) + \sum_{i=1}^{i=p} a_i y(t-i) + \sum_{i=0}^{i=m} b_i x(t-i) + \sum_{i=1}^{i=n} c_i y(t-i) + w(t)$$

which can be rewritten as $$y(t) = e'(t) + \sum_{i=1}^{i=p'} a'_i y(t-i) + \sum_{i=0}^{i=m} b_i x(t-i)$$

where p'=max(p,n), e'(t)=e(t)+w(t), $a'_i = a_i + c_i$ and $c_i$ or $a_i = 0$ for min(p,n)<i≦max(p,n). Thus, the form of the equation for the unrecognized feedback path looks the same as that for the original model, so the two possibilities cannot be distinguished without further information or assumptions. Of course, with the incorporation of additional assumptions or constraints it may be possible to identify additional features of the system such as the blood pressure-blood pressure feedback loop, and this would be within the scope of the proposed invention.

Figure 2:
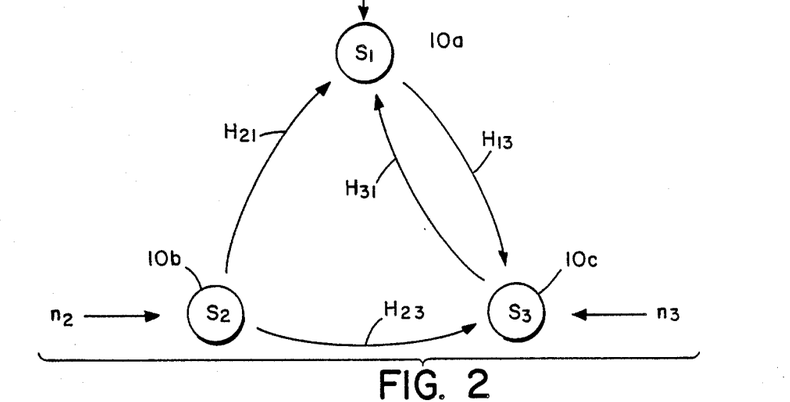
FIG. 2 is a block diagram of the interaction between the cardiac (10a), respiratory (10b), and vascular (10c) subsystems, indicating the parameters, transfer functions, and noise sources.

FIG. 2 depicts the interactions between the cardiac 10a, respiratory 10b, and vascular 10c subsystems. The cardiac subsystem is monitored by the heart rate, the vascular subsystem by the blood pressure, and the respiratory subsystem by the instantaneous lung volume. The use of random-interval breathing inserts broadband noise $N_2$ into the respiratory subsystem 10b.

The respiratory subsystem 10b has an effect on the cardiac subsystem 10a as indicated by the variation in heart rate caused by breathing, termed the respiratory sinus arrhythmia. Hence, the transfer function $H_{21}$ is non-zero. Similarly, the cardiac subsystem 10a affects the vascular subsystem 10c by cardiac output, and so the transfer function $H_{13}$ is also non-zero. Since the blood pressure in the vascular subsystem 10c affects the cardiac subsystem 10a through the heart rate baroreflex, its transfer function $H_{31}$ is non-zero. Finally, the respiratory subsystem 10b affects the vascular subsystem 10c, and so its transfer function $H_{23}$ is non-zero. By introducing broad band noise $N_2$ into the respiratory subsystem 10b and measuring heart rate, arterial blood pressure, and instantaneous lung volume, the transfer functions $H_{13}$, $H_{31}$, $H_{23}$, and $H_{21}$ can be calculated. In addition, the power spectra of the noise sources $N_1$, $N_2$ and $N_3$ can be computed. Note that in FIG. 2, $N_2 = S_2$ indicating that none of the other signals feed back onto $S_2$. In spite of the reduction in the number of transfer functions to be identified in the FIG. 2 model relative to the FIG. 1 model, the three noise sources must be linearly independent and their correlation must be known and parametrized in order to calculate unbiased transfer function estimates.

Figure 3:
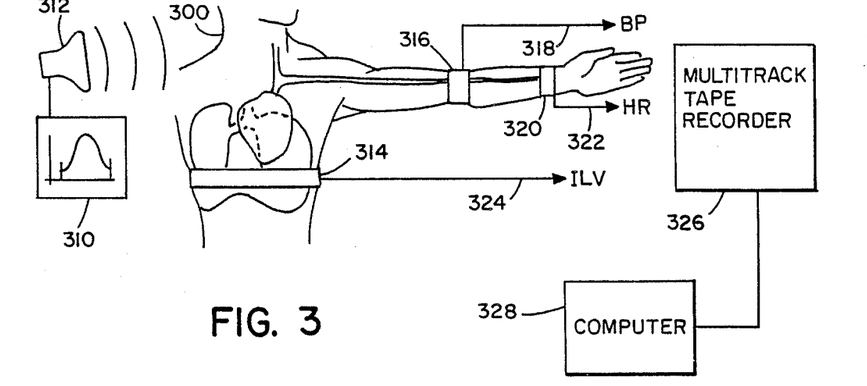
FIG. 3 is a schematic diagram of an apparatus with which the transfer functions shown in FIG. 2 can be determined.

One embodiment of a system to make these measurements is depicted in FIG. 3. A computer 310 generates a series of audio-pulses 312, which are spaced in time randomly in a given distribution (See *Transfer Function Analysis of Autonomic Regulation II—Respiratory Sinus Arrhythmia*, J. P. Saul, R. D. Berger, M. H. Chen, R. J. Cohen, American Journal of Physiology Vol. 256, (Heart Circ. Physiology 25) p. H153–H161 (1988), and U.S. Pat. No. 4,777,960—copies attached and incorporated herein by reference). In this embodiment the cues were distributed according to a Poisson distribution modified so that extremely short (less than 1 sec.) or long (greater than 15 sec.) intervals did not occur and so the subject would not feel discomfort. The exact distribution is not important; what matters is that the resulting instantaneous lung volume signal have energy over the entire range of relevant frequencies. In the case of circulatory regulation, the desired frequency range is 0.0–0.5 Hz. When the subject 308 hears the audio-cue, the subject inhales and exhales. It should be apparent that audio-cues are not required and that any sensory-cues generated by the computer would function as well. The instantaneous lung volume 324 is measured using a two-belt, chest-abdomen inductance plethysmograph 314 (Respitrace Systems) and recorded by a 8 channel FM tape recorder 326 (Hewlett-Packard 3968A). Similarly, the heart rate 322 is determined by a surface electrocardiogram device 320 and recorded by the 8 channel FM tape recorder 326. The blood pressure 318 is similarly measured 316 (using an intra-arterial catheter or continuous noninvasive blood pressure transducer) and recorded. The data is then analyzed using a computer 328.

Figure 4:
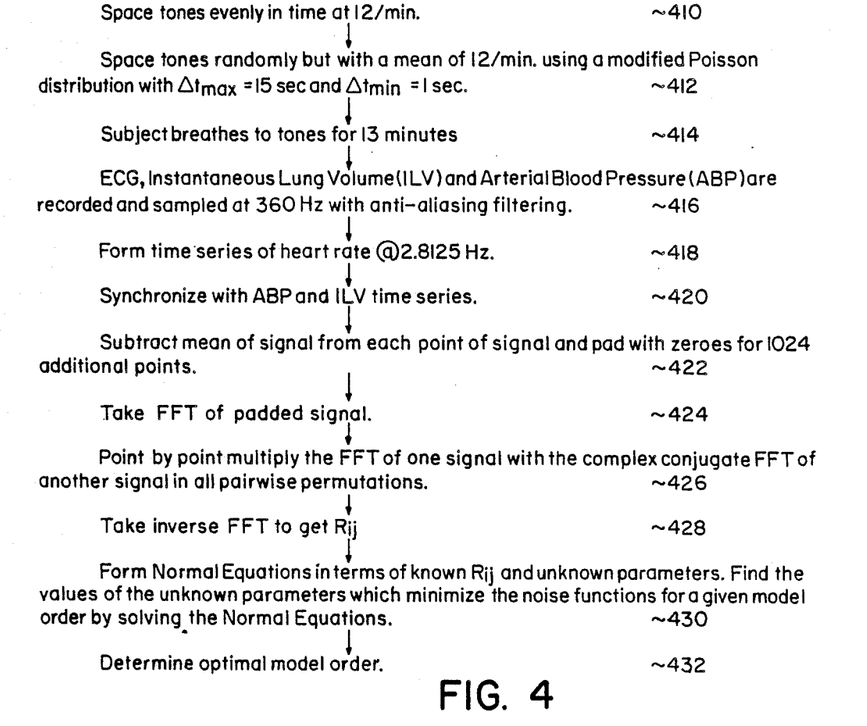
FIG. 4 is a flow diagram of the algorithm for determining the transfer functions of the system of FIG. 2.

FIG. 4 is a flow diagram of the steps required to estimate the transfer functions shown in FIG. 3. The subject is connected to one lead of an electrocardiogram monitor, a blood pressure monitor, and an instantaneous lung volume device and is asked to breathe in synchrony with a series of tones spaced evenly in time, at 12 breaths/minute 410. The random tone pattern is then used 412 and the subject asked to breath in synchrony with this prerecorded random distribution 414. While the subject is so breathing, the electrocardiogram, instantaneous lung volume, and blood pressure are recorded 416 on a 8-track F.M. tape recorder for later computer analysis.

The single lead electrocardiogram, blood pressure, and lung volume signals are digitized into 12 bits sampled at 360 Hz. The lung volume and electrocardiogram are filtered, sampled, and decimated to produce synchronous 3 hz discrete-time signals 420. These digitized signals are divided into 1024 point sequences for analysis.

The mean of the sequence is subtracted from each point, and each sequence is padded with 1024 additional samples of zero amplitude 422 to allow the use of the fast Fourier transform in computing the covariance of the sequence. The Fast Fourier Transform (FFT) is then taken of each padded sequence 424. Next, all the pair-wise permutations of the Fast Fourier Transform of one signal and the complex conjugate FFT of a second signal are multiplied point by point 426. That is, for example, the FFT of the heart rate signal is point by point multiplied by the complex conjugate FFT (FFT*) of the heart rate signal to generate one pair. Next, the FFT of the heart rate signal is multiplied by the blood pressure signal to generate another pair, and so on. So that:

$$F_{kq_i} F_k^* q_j = \text{Pair}_{ij}$$

for i, j = heart rate, blood pressure lung volume

The inverse Fast Fourier Transform of each pair yields the covariance estimate $\tilde{R}_{ij}(k)$ for each pair 428:

$$F_k^{-1} [\text{Pair}_{ij}] = \tilde{R}_{ij}(k)$$

Once the covariance estimates are determined, it becomes simply a matter of solving a set of normal equations to determine the transfer functions.

Specifically, the output of signal (y) at time (t) (y(t)) is determined by the output of signal (y) at earlier times (t−i), the input signals (x) at the earlier times (t−i), and the intrinsic noise of the signal $n_y$ at the time(t):

$$y(t) = n_y(t) + \sum_{i=1}^{i=p} a_i y(t-i) + \sum_{\text{inputs } j} \sum_{i=0}^{i=m_j} b_{ji} x_j(t-i)$$

That is, each output y(t) is explained as the sum of inputs $x_j(t)$ filtered through a transfer plus a noise source. The transfer function between $x_j(t)$ and y(t) is specified by the parameters $\{a_i\}$ and $\{b_{ji}\}$ for particular model orders ($m_j$) and (p). For each set of model orders ($m_j$), p, there is a set of optimal parameter values.

We calculate the optimal values by rearranging the above equation to isolate the noise term:

$$n_y(t) = y(t) - \sum_{i=1}^{i=p} a_i y(t-i) - \sum_{\text{inputs } j} \sum_{i=0}^{i=m_j} b_{ji} x_j(t-i)$$

By squaring both sides of the preceeding equation, one can express $n_y^2(t)$ as a function of the parameters and various quadratic terms of the data (e.g.: x(t−i)y(t−j), x(t−i)x(t−j), y(t−i)y(t−j) etc.) as follows:

$$n_y^2(t) = y^2(t) - \sum_{j=1}^{j=p} \sum_{i=1}^{i=p} a_i a_j y(t-i) y(t-j) +$$

$$\sum_{\text{inputs } k} \sum_{\text{inputs } j} \sum_{l=0}^{l=m_k} \sum_{i=0}^{i=m_j} b_{ji} b_{kl} x_j(t-i) x_k(t-l) -$$

$$2 \sum_{i=1}^{i=p} a_i y(t) y(t-i) - 2 \sum_{\text{inputs } j} \sum_{i=0}^{i=m_j} b_{ji} y(t) x_j(t-i) +$$

$$2 \sum_{i=1}^{i=p} \sum_{\text{inputs } j} \sum_{k=0}^{k=m_j} a_i b_{jk} y(t-i) x_j(t-k)$$

The cross-covariance estimate is defined by:

$$R_{uv}(T) = \frac{1}{N} \sum_{i=0}^{i=N-1} u(i+T) v(i)$$

Where N is the total number of data points. One can sum equation for $n_y^2(t)$ over all the data points, enabling one to substitute for the quadratic terms using the equation for the covariance estimate.

$$\frac{1}{N} \sum_{t=0}^{t=N-1} n_y^2(t) = R_{yy}(0) - \sum_{j=1}^{j=p} \sum_{i=1}^{j=p} a_i a_j R_{yy}(i-j) +$$

$$\sum_{\text{inputs } k} \sum_{\text{inputs } j} \sum_{l=0}^{l=m_k} \sum_{i=0}^{i=m_j} b_{jl} b_{kl} R_{xjxk}(l-i) -$$

$$2 \sum_{i=1}^{i=p} a_i R_{yy}(i) - 2 \sum_{\text{inputs } j} \sum_{i=0}^{i=m_j} b_{ji} R_{yxj}(i) +$$

$$2 \sum_{i=1}^{i=p} \sum_{\text{inputs } j} \sum_{k=0}^{k=m_j} a_i b_{jk} R_{yxj}(k-i)$$

In the above equation, the cross-covariance estimates $\bar{R}_{jik}$ are calculated from the data. Only the parameters $\{a_i\}$, $\{b_{ji}\}$ are unknown. In finding values for the parameters, one desires to minimize $$\sum_{t=0}^{t=N} n_y^2(t);$$

a necessary condition is that $$\frac{\partial}{\partial c} \sum_{t=0}^{t=N} n_y^2(t) = 0$$

where c is any of the parameters $\{a_i\}$, $\{b_{ji}\}$ 430. Thus, there is one equation expressing the necessary condition for each unknown parameter. Solving these linear equations (normal equations) simultaneously gives the optimal parameter values.

These parameters ($a_i$, $b_i$) minimize the noise function for a particular order for a given output. This calculation is repeated for other model orders until the optimum set of model orders is found 432. For example, one could optimize with respect to the Akaike Information Criteria. (See *A New Look at Statistical Model Identification*, Akaike, IEEE, Transactions on Automatic Control, PAC-19 p. 716–723 (1974)). The values of the parameters ($a_i$, $b_i$) which minimize this function for this order uniquely specified the transfer functions.

In one embodiment, the parametric equations relating heart rate (HR), blood pressure (BP), and instantaneous lung volume (ILV) are:

$$HR(t) = N_{HR}(t) + \sum_{i=i}^{m_1} a_i HR(t-i) + \sum_{i=0}^{m_2} b_i BP(t-i) +$$

$$\sum_{i=0}^{m} r_i ILV(t-i)$$

$$BP(t) = N_{BP}(t) + \sum_{i=1}^{n_1} a_i Br(t-i) + \sum_{i=0}^{n_2} b_i HR(t-i) +$$

$$\sum_{i=0}^{n_3} r_i ILV(t-i)$$

Since respiration is being modulated to generate broad-band noise, ILV is assumed not to be influenced by blood pressure and heart rate, and so will not have an equation describing it.

Figure 5:
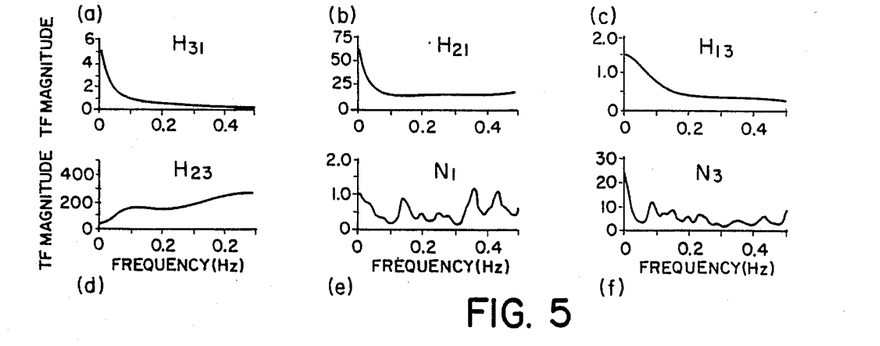
FIG. 5 shows the results of applying the algorithm of FIG. 4 to the system of FIG. 2.

FIG. 5 shows the results of the procedure described here. Using lung volume, arterial blood pressure and heart rate data from a healthy human subject, the transfer functions and noise sources (FIG. 2) were identified. The frequency response estimates for the transfer functions and the power spectra of the noise sources are displayed. Note that for linear, time-invariant systems, one can specify a transfer function by either its impulse response or its frequency response since either is a unique and complete specification of the transfer function. In the case where the transfer function is parametrized, the set of parameters is yet a third complete and unique specification of the transfer function. Thus, given any of these three specifications for a transfer function, one can calculate the other two. Accurate closed-loop identification of these transfer functions has not previously been possible using techniques from the prior art.

Figure 6:
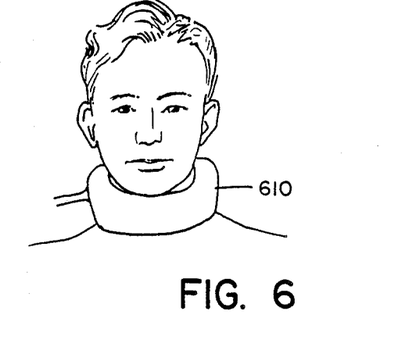
FIG. 6 is a schematic diagram of another embodiment of the invention used to determine the transfer functions of the system of FIG. 2.

Another embodiment of a method of determining transfer functions that introduces a broad-band exogenous input is the use of a neck suction chamber FIG. 6. By changing pressure in the chamber 610, the tissues in the neck are stretched.

Therefore, the chamber simulates the carotid sinus stretch, mimicking an increase in arterial blood pressure and thereby inducing reflex vasodilation and bradycardia. A full description of the use of the neck chamber can be found in U.S. Pat. No. 4,777,960.

Figure 7:
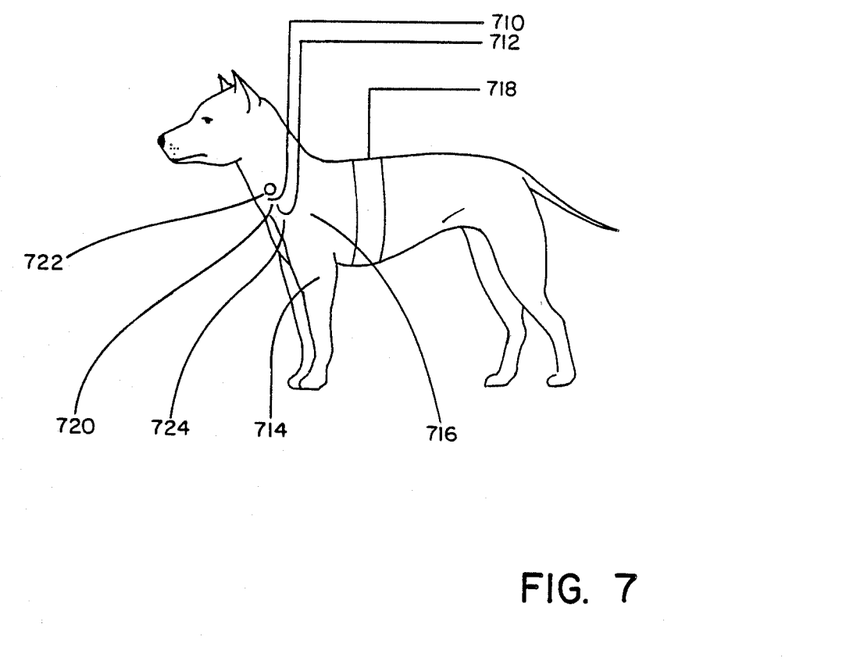
FIG. 7 is a schematic diagram of an embodiment of the invention useful in determining the transfer functions of the system of FIG. 2 in experimental animals.

An additional embodiment useful in non-human measurements is shown in FIG. 7. In this embodiment, experimental animals (dogs or sheep, for example) are instrumented to allow the recording of surface ECGs, (atrial 710 or ventricular 712), arterial blood pressure 714, central venous blood pressure 716, respiration 718, and cardiac output 720. In this embodiment external exogenous noise is introduced either by aortic cuff 722 wherein pressure applied to the aorta changes the cardiac output or by direct ventricular stimulation 724 which directly affects the heart rate.

Another embodiment of the invention involves analysis of four signals: heart rate, arterial blood pressure, instantaneous lung volume, and vascular resistance. Vascular resistance may be estimated (within a proportionality constant) by a nonlinear transformation of the arterial blood pressure signal. By fitting the diastolic decay of arterial blood pressure to an exponential form, the decay constant of this exponential may be computed for each beat. This decay constant is proportional to the vascular resistance. Alternatively, if cardiac output is measured continuously (as can be done in animal studies), vascular resistance may be computed on a beat-to-beat basis by dividing the average arterial pressure in a beat by the cardiac output in that beat (stroke volume). In this embodiment one computes transfer functions between the various signals, and one can compute the noise signals and their power spectra. In particular, the arterial blood pressure to vascular resistance transfer function provides a quantitative measure of the Resistance Baroreflex, whereas the arterial blood pressure to heart rate transfer function provides a quantitative measure of the Heart Rate Baroreflex.

Further embodiments exploit different perturbations to the cardiovascular system. One can place the patient on a tilt table. Tilting the patient from horizontal to vertical causes gravity to pull blood from the upper to lower body. In response, the patient's sympathetic nervous system is activated and vagal tone is withdrawn. One can use the tilt table to change the patient's physiologic state, which would then be identified by introducing a broad-band stimulus of some kind (such as random interval breathing). Alternatively, one could use rapid tilting as the primary stimulus. Lower body negative pressure, postural changes (for example, the patient stands up on his own), and exercise (treadmill, bicycle) can be used in a similar way: either as means of changing physiologic state in conjunction with broad-band perturbation or as broad-band perturbations themselves.

Of course, although each exogenous input has been described as a separate embodiment, it is possible to use multiple exogenous inputs in conjunction.

Having shown the preferred embodiments, those skilled in the art will realize many variations are possible which will still be within the scope and spirit of the claimed invention. Therefore, it is the intention to limit the invention only as indicated by the scope of the claims.

What is claimed is:

1. A method for analyzing a biological or physiological system comprising the steps of:
   A. Applying at least one exogenous broad-band perturbation to said physiological or biological system;
   B. Measuring m signals from the biological or physiological system;
   C. Transforming the m signals to generate a new set of n signals where n may be greater than, equal to or less than m;
   D. Representing the relationships between the new signals by causal transfer functions and additive noise sources; and
   E. Using a parametric system identification technique to characterize quantitatively at least two causal transfer functions and the noise sources.

2. The method of claim 1 wherein the quantitative characterization includes the selection of an optimal model order for the causal transfer function according to determined criteria.

3. The method of claim 1 where the parametric identification technique is an autoregressive-moving average, parametrization with a plurality of known exogenous inputs.

4. The method of claim 1 wherein said new signals are heart rate, arterial blood pressure, and instantaneous lung volume.

5. The method of claim 4 wherein said at least one broad-band perturbation is applied to the respiratory system.

6. The method of claim 5 wherein said at least one broad-band perturbation is applied to said respiratory system by random interval breathing.

7. The method of claim 4 wherein said at least one broad-band perturbation is applied to the cardiac system.

8. The method of claim 7 wherein said at least one broad-band perturbation is applied to said cardiac system by direct random ventricular stimulation.

9. The method of claim 1 wherein said new signals are heart rate, arterial blood pressure, arterial resistance and instantaneous lung volume.

10. The method of claim 1 wherein one measured signal is arterial blood pressure measured by intra-arterial catheter.

11. The method of claim 1 wherein one measured signal is arterial blood pressure measured by continuous noninvasive arterial blood pressure transducer.

12. The method of claim 1 wherein one measured signal is cardiac output.

13. The method of claim 1 wherein one measured signal is central venous pressure.

14. The method of claim 1 wherein said at least one broad-band perturbation is introduced into a physiological system of an organism by conscious acts by said organism.

15. The method of claim 14 wherein said conscious acts are induced by sensory-cues.

16. The method of claim 15 wherein said sensory-cues are aural.

17. The method of claim 15 wherein said sensory-cues are visual.

18. The method of claim 15 wherein said sensory-cues are tactile.

19. The method of claim 1 where said at least one broad-band perturbation is introduced by changes in posture.

20. The method of claim 1 where said at least one broad-band perturbation is introduced by changes in lower body negative pressure.

21. The method of claim 1 where said at least one broad-band perturbation is introduced by changes in body tilt.

22. The method of claim 1 where said at least one broad-band perturbation is introduced by exercise.

23. The method of claim 1 wherein said at least one broad-band perturbation has a Poisson distribution.

24. The method of claim 23 wherein said Poisson distribution is modified to have a maximum value.

25. The method of claim 24 wherein said maximum value is approximately 15 sec.

26. The method of claim 23 wherein said Poisson distribution is modified to have a minimum value.

27. The method of claim 26 wherein said minimum value is approximately 1 sec.

28. The method of claim 1 wherein said at least one broad-band perturbation has a Gaussian distribution.

29. The method of claim 1 wherein the representation of the interaction between the n signals results in $n(n-1)$ transfer functions and n additive noise sources.

30. The method of claim 1 wherein the representing of the interaction between the n signals includes the removal of transfer functions and noise sources known to be of negligible significance.

31. The method of claim 1 applied to several physiological states.

32. The method of claim 31 wherein changes of physiological state are induced by changing posture.

33. The method of claim 31 wherein changes of physiological state are induced by changes in lower body pressure.

34. The method of claim 31 wherein changes of physiological state are induced by changes in body tilt.

35. The method of claim 31 wherein changes of physiological state are induced by exercise.

36. The method of claim 1 wherein at least one signal transformation is nonlinear.

37. The method of claim 1 wherein at least one signal transformation is linear.

38. A system for analyzing a biological or physiological system comprising:
   A. An apparatus adapted to introduce at least one exogenous broad-band pertubation to said physiological or biological system;
   B. An apparatus adapted to measure m signals from said physiological or biological system; and
   C. A computing apparatus programmed to i. Transform said m signals to generate a new set of n signals;
 ii. Represent the relationships between the new n signals by causal transfer functions and additive noise sources; and
 iii. Characterize quantitatively at least two causal transfer functions and the noise sources.

39. The system of claim 38 wherein said signals are measured by electrocardiograph apparatus, radial artery catheter apparatus and plethysmograph apparatus.

40. The system of claim 39 wherein said plethysmograph is a two-belt inductance plethysmograph apparatus.

41. A method for analyzing transfer functions and noise sources for heart rate, arterial blood pressure and respiration in an organism, comprising the steps of:
 A. Applying broad-band perturbation by random interval breathing and/or random interval neck suction;
 B. Measuring the electrocardiogram, arterial blood pressure and respiration signals;
 C. Deriving a heart rate signal by nonlinear transformation of the electrocardiogram or arterial blood pressure signal;
 D. Representing the relationship between the heart rate, arterial blood pressure and respiration signals by causal transfer functions and additive noise sources; and
 E. Using parametric system identification to characterize quantitatively at least two causal transfer functions and the noise sources.

42. A method for analyzing transfer functions and noise sources for heart rate, arterial blood pressure, vascular resistance and respiration in an organism, comprising the steps of:
 A. Applying broad-band perturbation by random interval breathing and/or random interval neck suction;
 B. Measuring the electrocardiogram, arterial blood pressure and respiration signals;
 C. Deriving a heart rate signal by nonlinear transformation of the electrocardiogram or arterial blood pressure signal, and deriving a vascular resistance signal by nonlinear transformation of the arterial blood pressure signal;
 D. Representing the relationship between the heart rate, arterial blood pressure, vascular resistance, and respiration signals by causal transfer functions and noise sources; and
 E. Using parametric system identification to characterize quantitatively at least two causal transfer functions and the noise sources.

\* \* \* \* \*

UNITED STATES PATENT AND TRADEMARK OFFICE
CERTIFICATE OF CORRECTION

PATENT NO. : 4,930,517

DATED : June 5, 1990

INVENTOR(S) : Richard J. Cohen, et al.

It is certified that error appears in the above-identified patent and that said Letters Patent is hereby corrected as shown below:

```
Column 1, line 32:   change "any" to -- may --.
Column 2, line 42:   change "Ceruttie" to -- Cerutti --.
Column 3, line 64:   change "transfer," to -- transfer --.
Column 5, line 6:    change "purpose" to -- purposes --.
          line 23:   change "H_{ij})" to -- H_{ij} --.
Column 8, line 34:   after "transfer" add -- function --.
```

Signed and Sealed this

Twentieth Day of August, 1991

Attest:

HARRY F. MANBECK, JR.

*Attesting Officer*

*Commissioner of Patents and Trademarks*